US012635947B1

(12) United States Patent
Ghaus et al.

(10) Patent No.: US 12,635,947 B1
(45) Date of Patent: May 26, 2026

(54) DEVICE AND METHOD FOR TREATMENT OF ASTHMA AND CROHNS SYMPTOMS

(71) Applicant: Pine-Ananas ITC LLC, Ashburn, VA (US)

(72) Inventors: Amisi Ghaus, Ashburn, VA (US); Kiana Ghaus, Ashburn, VA (US)

(73) Assignee: Pine-Ananas ITC LLC, Ashburn, VA (US)

( * ) Notice: Subject to any disclaimer, the term of this patent is extended or adjusted under 35 U.S.C. 154(b) by 0 days.

(21) Appl. No.: 19/324,446

(22) Filed: Sep. 10, 2025

(51) Int. Cl.
| | |
|---|---|
| *A61B 5/00* | (2006.01) |
| *A61B 5/053* | (2021.01) |
| *A61B 5/08* | (2006.01) |
| *A61B 5/145* | (2006.01) |
| *G06N 20/00* | (2019.01) |

(52) U.S. Cl.
CPC ............ *A61B 5/6833* (2013.01); *A61B 5/053* (2013.01); *A61B 5/0803* (2013.01); *A61B 5/082* (2013.01); *A61B 5/14514* (2013.01); *A61B 5/7275* (2013.01); *G06N 20/00* (2019.01); *A61B 2562/0271* (2013.01)

(58) Field of Classification Search
CPC ..... A61B 5/6833; A61B 5/053; A61B 5/0803; A61B 5/082; A61B 5/14514; A61B 5/7275; A61B 2562/0271; G06N 20/00
See application file for complete search history.

(56) References Cited

U.S. PATENT DOCUMENTS

| | | | |
|---|---|---|---|
| RE34,938 E | * | 5/1995 | Serikov ................. A61B 5/091 |
| | | | 600/537 |
| 8,591,430 B2 | * | 11/2013 | Amurthur .......... A61B 5/14551 |
| | | | 600/529 |
| 10,279,106 B1 | | 5/2019 | Cook et al. |
| 2007/0224084 A1 | * | 9/2007 | Holmes ............ A61B 5/150022 |
| | | | 422/50 |
| 2011/0184302 A1 | * | 7/2011 | Eschler .................... A61B 5/08 |
| | | | 600/529 |
| 2011/0314896 A1 | * | 12/2011 | Carlson ................. A61B 5/411 |
| | | | 73/23.3 |
| 2018/0052084 A1 | * | 2/2018 | Jones ..................... G01N 1/405 |
| 2023/0329636 A1 | * | 10/2023 | Ramp .................... G16H 40/63 |
| 2025/0040836 A1 | * | 2/2025 | Heikenfeld .......... A61B 5/1455 |

OTHER PUBLICATIONS

Kuenzig, et al., "Co-occurrence of Asthma and the Inflammatory Bowel Diseases: A Systematic Review and Meta-1 analysis", Clinical and Translational Gastroenterology (2018)9:188, Sep. 24, 2018.

* cited by examiner

*Primary Examiner* — Scott M. Getzow

(57) ABSTRACT

A device and method for minimizing asthma and/or Crohn's or IBD. The device comprises a user-wearable device comprising: a micro-electro-mechanical systems (MEMS) microphone system; a bioelectrical impedance analysis system; a breath humidity and breath temperature sensor system; an interstitial fluid monitoring system; at least one processor; a power system that powers the at least one processor, the at least one electronic communications system, and the systems of the user-wearable device; and wherein the electronic communication system may receive data from at least one other electronic system that carries instructions for a treatment plan that is refined over time via machine learning.

6 Claims, 7 Drawing Sheets

GNRs
AuNPs
Nafion

NO  NO$_2$

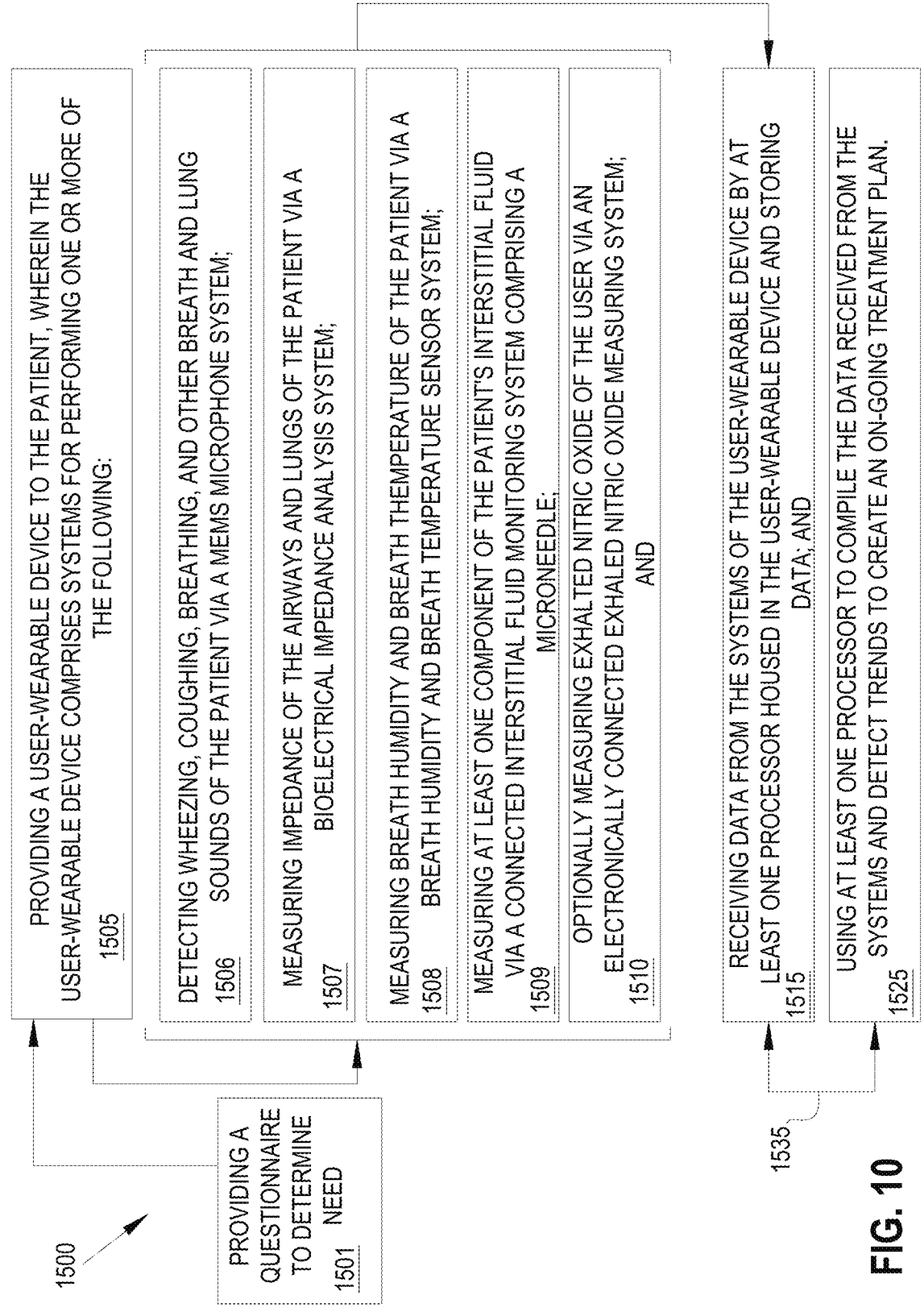

PROVIDING A USER-WEARABLE DEVICE TO THE PATIENT, WHEREIN THE USER-WEARABLE DEVICE COMPRISES SYSTEMS FOR PERFORMING ONE OR MORE OF THE FOLLOWING:

1505

DETECTING WHEEZING, COUGHING, BREATHING, AND OTHER BREATH AND LUNG SOUNDS OF THE PATIENT VIA A MEMS MICROPHONE SYSTEM;

1506

MEASURING IMPEDANCE OF THE AIRWAYS AND LUNGS OF THE PATIENT VIA A BIOELECTRICAL IMPEDANCE ANALYSIS SYSTEM;

1507

MEASURING BREATH HUMIDITY AND BREATH THEMPERATURE OF THE PATIENT VIA A BREATH HUMIDITY AND BREATH TEMPERATURE SENSOR SYSTEM;

1508

MEASURING AT LEAST ONE COMPONENT OF THE PATIENT'S INTERSTITIAL FLUID VIA A CONNECTED INTERSTITIAL FLUID MONITORING SYSTEM COMPRISING A MICRONEEDLE;

1509

OPTIONALLY MEASURING EXHALTED NITRIC OXIDE OF THE USER VIA AN ELECTRONICALLY CONNECTED EXHALED NITRIC OXIDE MEASURING SYSTEM; AND

1510

PROVIDING A QUESTIONNAIRE TO DETERMINE NEED

1501

RECEIVING DATA FROM THE SYSTEMS OF THE USER-WEARABLE DEVICE BY AT LEAST ONE PROCESSOR HOUSED IN THE USER-WEARABLE DEVICE AND STORING DATA; AND

1515

USING AT LEAST ONE PROCESSOR TO COMPILE THE DATA RECEIVED FROM THE SYSTEMS AND DETECT TRENDS TO CREATE AN ON-GOING TREATMENT PLAN.

DEVICE AND METHOD FOR TREATMENT OF ASTHMA AND CROHNS SYMPTOMS

CROSS-REFERENCE TO RELATED APPLICATIONS

This application is an application for patent under 35 U.S.C. 111(a).

BACKGROUND

Asthma is a chronic respiratory disease where the airways become inflamed and narrowed, making it hard to breathe. Symptoms include wheezing, coughing, shortness of breath, and chest tightness. Asthma is a polygenic condition with different genes each contributing a small amount of risk. If parents or siblings have asthma, the risk of having asthma is higher. Variations in genes that regulate the immune response, including IL-4, IL-5, IL-13, and ORMDL3, can make people more prone to airway inflammation.

Certain autoimmune and immune-related conditions can contribute to asthma symptoms or make asthma worse, even though asthma itself is not classified as a "classic autoimmune disease." rheumatoid arthritis (RA), systemic lupus erythematosus (SLE), autoimmune thyroid disease, or Hashimoto's or Graves' Disease, Celiac Disease, and other autoimmune gut disorders, eosinophilic granulomatosis with polyangiitis (EGPA) formerly known as Churg-Strauss, psoriasis, psoriatic arthritis, Crohn's disease or inflammatory bowel disease (IBD) can also contribute and worsen the asthma symptoms.

Therefore, there is a need for patients with asthma and/or Crohn's disease or IBD to monitor and reduce asthma and Crohn's or IBD related symptoms to improve quality of life.

SUMMARY OF THE INVENTIONS

The present disclosure comprises device and method for minimizing asthma and/or Crohn's or IBD. The device comprises a user-wearable device comprising: a micro-electro-mechanical systems (MEMS) microphone system; a bioelectrical impedance analysis system; a breath humidity and breath temperature sensor system; an interstitial fluid monitoring system; at least one processor; a power system that powers the at least one processor, the at least one electronic communications system, and the systems of the user-wearable device; and wherein the electronic communication system may receive data from at least one other electronic system that carries instructions for a treatment plan that is refined over time via machine learning.

BRIEF DESCRIPTION OF THE DRAWINGS

The accompanying drawings form part of the disclosure and are incorporated into the subject specification. The drawings illustrate example embodiments of the disclosure and, in conjunction with the present description and claims, explain at least in part various principles, features, or aspects of the disclosure. Certain embodiments of the disclosure are described more fully below with reference to the accompanying drawings. However, various aspects of the disclosure may be implemented in many different forms and should not be construed as limited to the implementations set forth herein. Like numbers refer to like, but not necessarily the same or identical, elements throughout.

FIG. 10 presents an example method for treatment of asthma and Crohn's Disease using the example user-wearable device for monitoring user health data.

DETAILED DESCRIPTION

Figures 1, 2, 3:
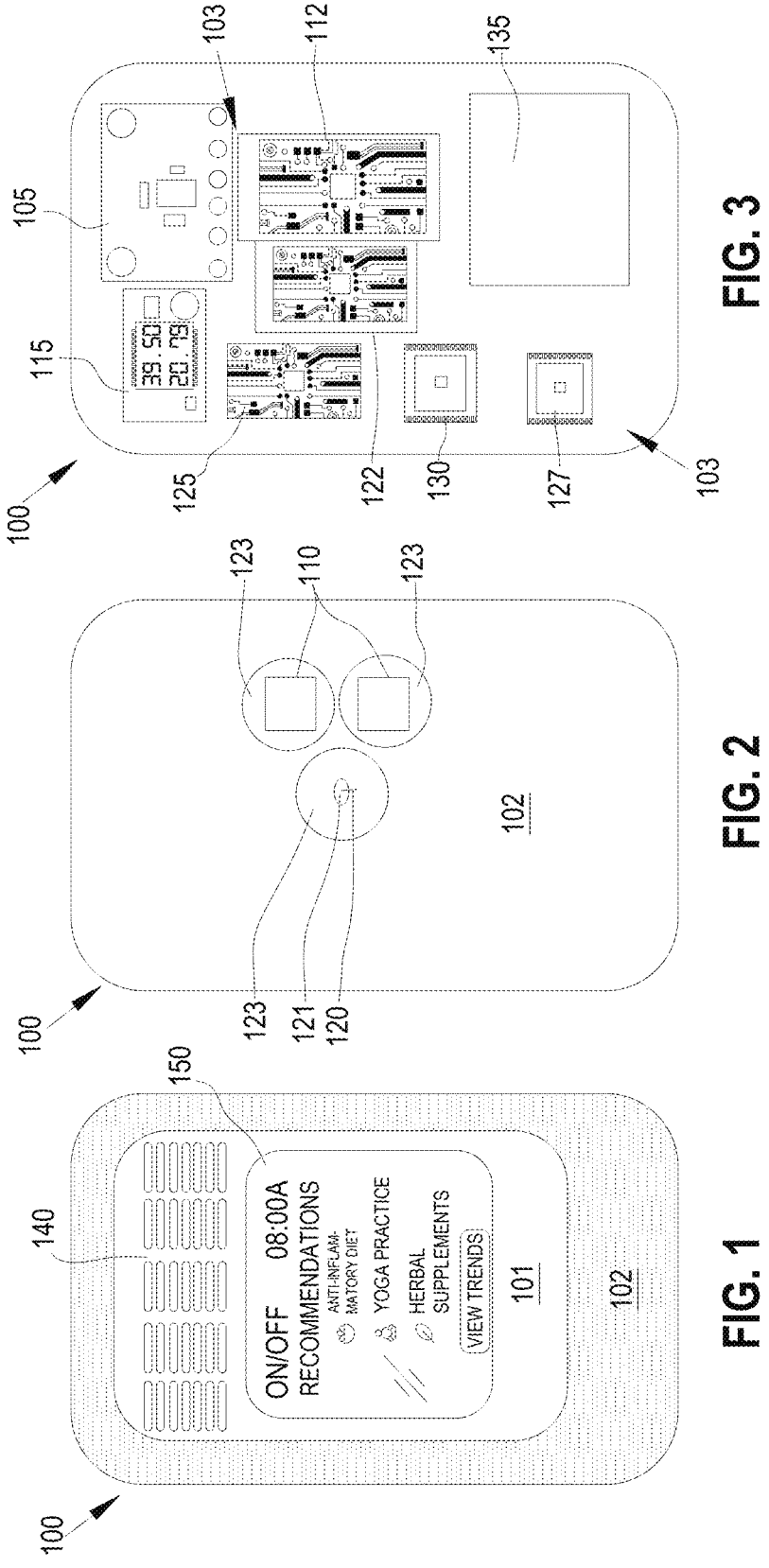
FIG. 1 presents the front side of an example user-wearable device for monitoring user health data.
FIG. 2 presents the back side of the example user-wearable device for monitoring user health data.
FIG. 3 presents the internal components of the example user-wearable device for monitoring user health data.

This disclosure provides, in at least some embodiments, systems, devices, and/or methods for monitoring and providing a treatment plan for a user with asthma and/or Crohn's Disease (CD) or inflammatory bowel disease (IBD). In some aspects, the present disclosure is drawn to a user-wearable device comprising: a micro-electro-mechanical systems (MEMS) microphone system for recording sounds related to breathing including at least one of taking a breath, labored breathing, wheezing, and coughing of a user; a bioelectrical impedance analysis system which produces an electrical current and measures impedance of the electrical current in the lungs; a breath humidity and breath temperature sensor system; an interstitial fluid monitoring system comprising at least one microneedle capable of taking a sample of interstitial fluid from the user; at least one processor, wherein the at least one processor comprises a processor and a memory for receiving data from the systems of the user-wearable device, storing data from the systems of the user-wearable device, controlling systems of the user-wearable device, and transmitting the received data to at least one electronic communications system programmed to transmit data to at least one other electronic system; a power system that powers the at least one processor, the at least one electronic communications system, and the systems of the user-wearable device; and wherein the at least one electronic communication system may receive data from at least one other electronic system that carries instructions for at least one of the at least one processor, the power system, and the systems of the user-wearable device. In some aspects, the user-wearable device further comprises an electronically connected exhaled breath nitric oxide measuring system.

In some aspects, the user-wearable device further comprises an electronically connected exhaled breath nitric oxide measuring system wherein the electronically connected exhaled breath nitric oxide measuring system comprises a fractional exhaled nitric oxide testing device or wherein the electronically connected exhaled breath nitric oxide measuring system comprises an electrochemical sensor capable of detecting nitric oxide.

In some aspects, the user-wearable device further comprises a tube connected between the user-wearable device and the microneedle and a patch comprising a temporary adhesive on one side, wherein the patch holds the microneedle in place in the user's skin. In some aspects, the user-wearable device comprises a bioelectrical impedance analysis system that measures lung impedance over time. In some aspects, the user-wearable device comprises a breath humidity and temperature sensor system that measures breath humidity and breath temperature over time. In some aspects, the user-wearable device comprises an interstitial fluid monitoring system wherein the interstitial fluid monitoring system detects and/or measures at least one of CRP, TNF-α, IL-6, and Calprotectin.

In some aspects, the user-wearable device comprises a processor that is a microcontroller unit (MCU) processor. In some aspects, the user-wearable device comprises a processor that is a system on a chip (SoC) processor. In some aspects, the user-wearable device collects data from the systems wherein data from each of the systems is compiled over time and, via at least one separate connected processor, the data, along with other user data, is used to detect trends in order to create an on-going treatment plan for managing at least one of asthma and Crohn's or inflammatory bowel diseases (IBD) using at least one of artificial intelligence (AI) and machine learning (ML). In some aspects, the data includes data from a fecal biomarker test of the user. In some aspects, other user data includes at least one of diet information, yoga practice, meditation practice, use of immune-modulating herbs, environmental exposures, fecal biomarker test data, and stress data.

In some aspects, the present disclosure comprises a method for treating at least one of asthma and Crohn's or inflammatory bowel disease (IBD) in a patient with need for treatment thereof, the method comprising the steps of: providing a user-wearable device to the patient, wherein the user-wearable device comprises systems for performing the following: detecting wheezing, coughing, breathing, and other breath and lung sounds of the patient via a MEMS microphone system; measuring impedance of the airways and lungs of the patient via a bioelectrical impedance analysis system; measuring breath humidity and breath temperature of the patient via a breath humidity and breath temperature sensor system; and measuring at least one component of the patient's interstitial fluid via a connected interstitial fluid monitoring system comprising a microneedle, wherein the one component is selected from at least one of CRP, TNF-α, IL-6, and Calprotectin; receiving and storing data from the systems of the user-wearable device by at least one processor housed in the user-wearable device; and using at least one processor, wherein the at least one processor comprises at least one of the at least one processor housed in the user-wearable device or at least one separate processor, to compile the data received from the systems and, via the at least one processor, the data, and other patient data, is used to detect trends to create an on-going treatment plan for managing at least one of asthma and Crohn's or IBD using at least one of artificial intelligence (AI) and machine learning (ML).

In some aspects, the method further comprises measuring exhaled nitric oxide of the user via an electronically connected exhaled nitric oxide measuring system via fractional exhaled nitric oxide testing device or an electrochemical sensor capable of detecting nitric oxide. In some aspects, the method further comprises a first step wherein the user supplies at least one of health data, health history, medication history, diet information, environmental exposure data, stress data, and lifestyle data to the at least one processor to determine whether the user needs a treatment for at least one of asthma and Crohn's or IBD. In some aspects, the on-going treatment plan comprises suggestions for implementation of at least one of diet changes, yoga practice, meditation practice, and use of immune-modulating herbs by the user. In some aspects, the method further comprises using the at least one processor to refine the on-going treatment plan based on data detected and measured following implementation of the on-going treatment plan via at least one of AI and ML. In some aspects, the method further comprises adding fecal biomarker data of the user to the data.

Figure 6:
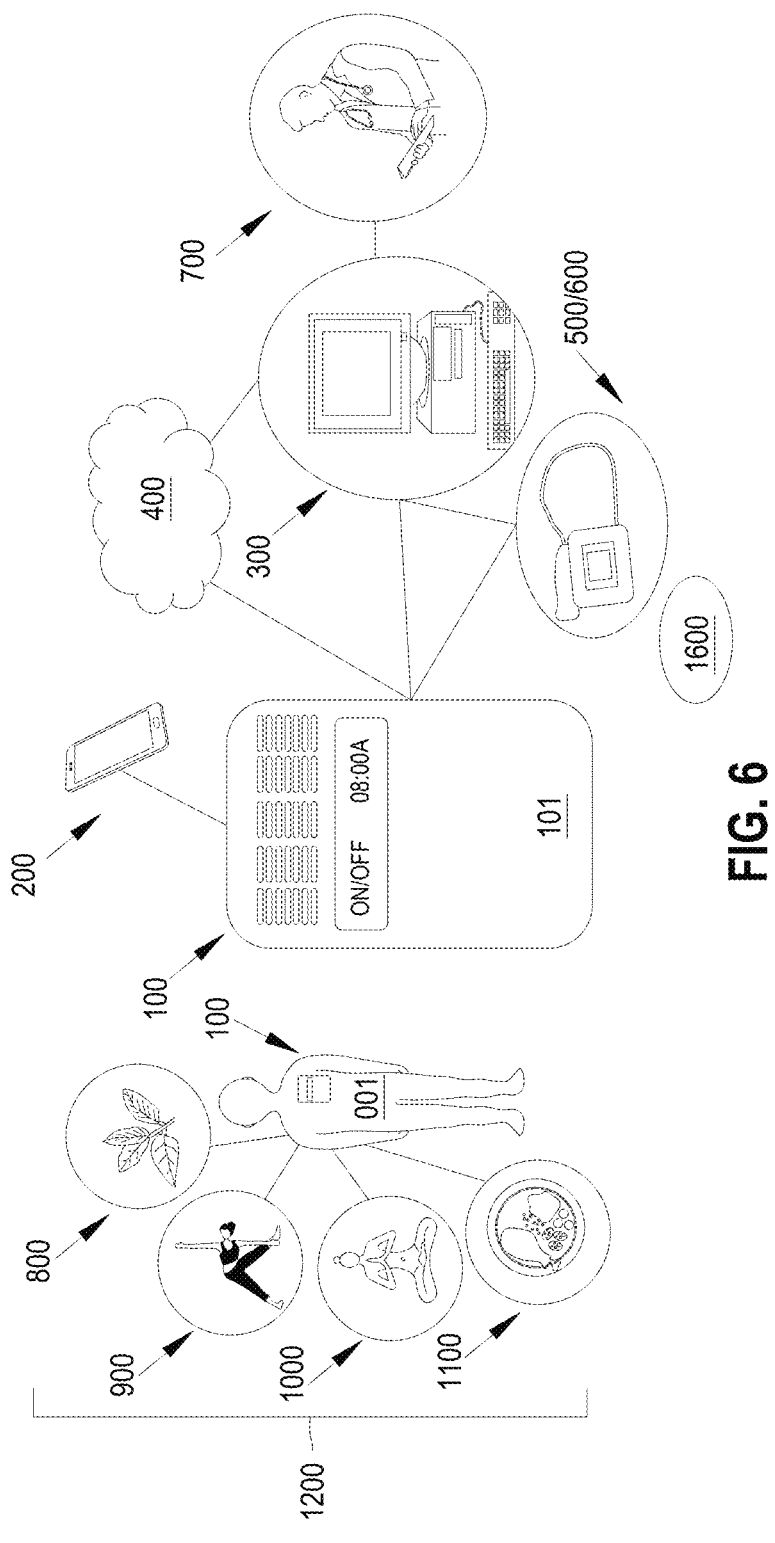
FIG. 6 illustrates an example environment of connectivity of the user-wearable device for monitoring user health data.

As presented in FIG. 1, the example user-wearable device 100 comprises a front cover 101 or housing that may include a graphics display 150, and vents 140 or openings to allow air passage into the interior compartment of the device FIG. 3, 103. An adhesive patch FIG. 1, 102 may be fitted to the user-wearable device 100 to adhere to skin (not shown) of a user. In other embodiments straps or bands of material, for example a fabric material may be fitted to the user-wearable device 100 to secure it to a user FIG. 6, 001. As is illustrated in FIG. 6, in preferred examples the user-wearable device 100 is secured to an upper chest area or upper arm area of a user 001.

As illustrated in FIG. 2, because of sensing components located on the back cover 102 of the user-wearable device 100, the user-wearable device 100 should contact the skin (not shown) of the user 001. In one embodiment, a microneedle 120 for sampling interstitial fluid of a user protrudes through a port 121 in the back cover of the user-wearable device 100. The port may be encircled or supported by a support piece 123 to hold the microneedle 120 in place. Although the port 121 and support piece 123 are represented as being round, these pieces may take various shapes as the design of the user-wearable device may require. Also present on the back cover 102 is a pair of electrodes 110 for measuring impedance, especially of the lungs and airways of the user. These electrodes 110 may also be enclosed or supported by support pieces 123 connected to or modeled into the back cover 102. The electrodes 110 and wiring (not shown), or other components of the electrodes may protrude through the support pieces 123 and/or back cover 102 of the user-wearable device 100 into the interior compartment FIG. 3, 103.

The interior compartment 103 of the user-wearable device 100 is presented in FIG. 3. An acoustic microphone or micro-electro-mechanical systems (MEMS) microphone system 105 for recording sounds related to breathing, including but not limited to wheezing, labored breathing, coughing, and taking a breath, may be positioned near the vents 140 or openings to detect sounds related to breathing and breathing patterns, and those described herein, of the user. A MEMS microphone 105 is a complete, sound-sensing system manufactured on a silicon wafer using semiconductor techniques. MEMS mics use a capacitive or piezoelectric sensing element to convert sound pressure into an electrical signal.

Internal components of the bioelectrical impedance analysis system 112 connected to the electrodes 110 being a part of the bioelectrical impedance analysis system 112, may be included in the interior compartment 103 of the user-wearable device 100 as illustrated in FIG. 3. The bioelectrical impedance analysis system 112 may measure the impedance of electrical current in the lungs and airways of the user by emitting through an electrode 110 a small electrical current and measuring through another electrode 110 a current returning to the user-wearable device 100.

Figure 4:
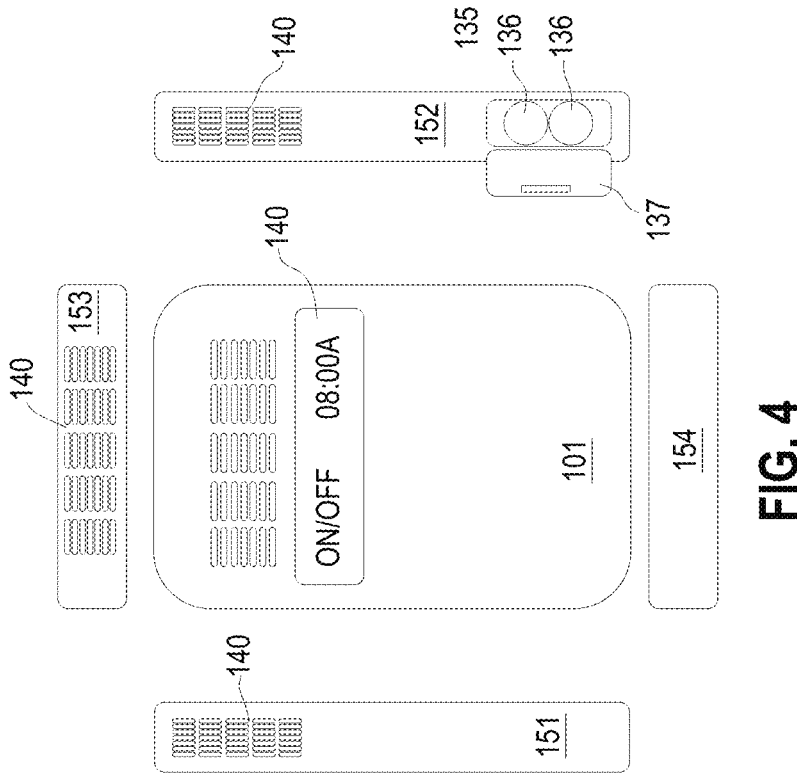
FIG. 4 illustrates the front, right, left, top, and bottom side views of the example user-wearable device for monitoring user health data.

Also included in the interior compartment FIG. 3, 103 is a breath humidity and temperature sensor system 115 for measuring a humidity and temperature of the breath of the user. The breath humidity and temperature sensor system 115 may be positioned near the vents 140 or openings of the device 100, as shown on the front 101 of the device in FIG. 1 and/or on the top 153 and/or sides 151, 152 of the device as shown in FIG. 4, to receive exhaled breath of the user. A breath humidity and temperature sensor system 115 measures the humidity and temperature of exhaled air, typically using a thermistor for temperature and an optical or nanoforest-based humidity sensor. A thermistor is often used for temperature measurement, which is a type of resistor whose resistance changes with temperature. By measuring this resistance and using a lookup chart or the Steinhart-Hart equation, temperature of the breath can be determined via digital programming. Optical sensors that use near-infrared light can measure moisture content, while other sensors use specialized porous materials that change their properties, like capacitance or resistance, in response to humidity.

Internal components of the interstitial fluid monitoring system 122 also comprising parts on the back 102, 120, 121, 123 that receives a sample of interstitial fluid from a microneedle FIG. 2, 120, on the exterior of the user-wearable device, enables sampling of user interstitial fluid (ISF) and testing for components of the ISF associated with asthma, Crohn's, and/or IBD, which may in an example include of C-reactive protein (CRP), TNF-α, IL-6, and Calprotectin. Sensors such as electrochemical impedance spectroscopy (EIS)-based systems and microneedle-based biosensors, may accurately quantify CRP and other pro-inflammatory cytokines, CRP, including hs-CRP, and proteins, like Calprotectin, as well as other inflammatory markers. Additional data may be integrated into a data set for a user FIG. 6, 001 including but not limited to fecal biomarker data FIG. 6, 1600, blood test data, and other lung and/or digestive system function data.

The interior compartment FIG. 3, 103 also comprises at least one processor 125 wherein the at least one processor 125 comprises a processor and a memory for receiving data from the systems 105, 110, 112, 115, 122 of the user-wearable device 100, storing data from the systems 105, 110, 112, 115, 122 of the user-wearable device 100, controlling systems 105, 110, 112, 115, 122, including the power source 135 and communications system 130 of the user-wearable device 100, and transmitting, via the communications system 130 the received data from the system sensors and detectors to at least one electronic communications system 130 programmed to transmit data to at least one other electronic system outside the user-wearable device 100. Examples of processors that may be suitable for application in the user-wearable device 100 of the present disclosure include but are not limited to a microcontroller unit (MCU) processor, also termed a microcontroller, that is a compact computer on a single chip that integrates a central processing unit (CPU), being a processor, memory, and input/output peripherals to control one or more specific function(s) in an embedded system. Unlike microprocessors, which are just a CPU, MCUs contain all the necessary components to run a program and operate a device. Another example of a processor that may be suitable for use in the user-wearable device 100 of the present disclosure includes a system on a chip (SoC) processor, being a complete computer system integrated onto a single integrated circuit or chip. It combines various components like the CPU, GPU, memory, and other peripherals onto one piece of silicon. This integration offers benefits like reduced size, lower power consumption, and improved performance compared to traditional multi-chip systems.

Other processor systems that may be utilized include but are not limited to ADC, an analog-to-digital converter (ADC), an electronic component that converts continuous analog signals, like voltage, into discrete digital values that microcontrollers and computers can process. An ADC component may be utilized in the detection and measurement systems especially in the bio-impedance electronics 112 and/or various electrochemical sensors 105, 115, 122, FIG. 7, 500. For AI and ML functions of the processor 125 an AI/ML edge accelerator 127 may be utilized. AI/ML edge accelerator 127 is a specialized hardware component designed to perform machine learning (ML) tasks directly on a local device, or at the "edge" of a network, rather than sending data to a central cloud server. These accelerators are optimized for high performance with low power consumption and latency.

Also included in the interior compartment FIG. 3, 103 is the power source 135 which may be a rechargeable battery, battery or batteries, or other power providing system to power the user-wearable device and all systems therein. Rechargeable battery examples include but are not limited to rechargeable Li—Po batteries, a type of lithium-ion battery that use a polymer electrolyte instead of a traditional liquid electrolyte. This semi-solid or solid polymer material allows for greater flexibility in the battery's shape and size, making Li—Po batteries ideal for many high-tech consumer electronics. The user-wearable device 100 may be designed with ultra-low power requirements, wherein the processor could transfer into a sleep mode to conserve power.

A wired or wireless communications system 130 provides the user-wearable device 100 with capability to send and receive data to and from the processor 125 or other systems. A wireless communication system 130 in a preferred embodiment may comprise a wireless communication chip 130 being an integrated circuit that enables devices to send and receive data without physical cables, acting as a bridge between radio, cellular, Bluetooth or other wireless signals and a device's digital electronics. These chips include radio frequency (RF) transceivers, signal processors, and power management components to support various protocols like Wi-Fi, Bluetooth, Bluetooth Low Energy (BLE) signal, NFC, or near field communication, a short-range wireless technology that enables communication between two electronic devices within a few centimeters of each other, and cellular signals. Other components to support powering, communication, and function of the systems not limited to wiring and other components that are necessarily included in the interior compartment 103 of the device as are required for design considerations may not be shown but would necessarily be included.

The various example embodiments of the disclosure may be operational with numerous other general purpose or special purpose computing system environments or configurations. Examples of well-known computing systems, environments, and/or configurations that may be suitable for implementation of various aspects or features of the disclosure in connection with the management of health professional communication in accordance with aspects described herein may comprise personal computers, server computers, laptop devices, handheld computing devices, such as mobile tablets or e-readers, wearable computing devices, and multiprocessor systems. Additional examples may include set-top boxes, programmable consumer electronics, network personal computers (PCs), minicomputers, mainframe computers, blade computers, programmable logic controllers, distributed computing environments that comprise any of the above systems or devices, and the like.

As described above and in alternate configurations, the example device FIG. 3, 100 may comprise one or more processors, one or more input/output (I/O) interfaces, a memory, and a bus architecture that functionally couples various functional elements of the device 100. In certain embodiments, the device 100 may include, optionally, a radio unit. The radio unit may include one or more antennas and a communication processing unit that may permit wireless communication between the device 100 and another device, as shown in FIG. 6, 200, 300, 400, 500/600, 1600 such as one of the computing device(s) 300 and/or a cloud network 400 enabling cloud computing, and smartphones or other mobile devices 200. The bus may include at least one of a system bus, a memory bus, an address bus, or a message bus, and may permit the exchange of information, whether data, metadata, and/or signaling, between the processor(s) 125 of the device 100, the I/O interface(s), and/or the memory, or respective functional elements therein. In certain scenarios, the bus, in conjunction with one or more internal programming interfaces, also referred to as interface(s), may permit such exchange of information. In scenarios in which the processor(s) 125 include multiple processors, the computing device may utilize parallel computing.

The front cover 101 and back cover 102 of the user-wearable device, as illustrated in FIGS. 1-2, and 4, along with top 153, right 151, left 152, and bottom 154 sides, may be a single molded piece, or at least two molded pieces fit together. The covers 101, 102, side pieces 151-152, and top and bottom pieces 153-154 may be made of an appropriate material such as a plastic, being a medical grade plastic appropriate for skin contact, for example a medical grade silicone. The adhesive (not shown) of the patch 102 would also be comprised of a semi-permanent adhesive appropriate for skin contact. The front cover 101 and back cover 102 of the user-wearable device, as illustrated in FIGS. 1-2, and 4, along with top 153, right 151, left 152, and bottom 154 sides may be fashioned into various shapes including but not limited to a rectangle, square, oval, circular, or any shape that serves to fit the design and architecture of the interior components and systems.

As shown in FIG. 6, the electronic communications system FIG. 3, 130 or I/O interface(s) may permit communication of information between the example device 100 and an external device FIG. 6, 200, 300, such as another computing device 300, or a network element 400, being a cloud based computing environment, or a user device 200, such as a phone, tablet, or other computing device having communication ability. Such communication may include direct communication or indirect communication, such as the exchange of information between the device 100 and a cloud network 400 or external device 200, 300 via a network or elements thereof. The electronic communications system FIG. 3, 130 or I/O interface(s) may comprise one or more of network adapter(s) or peripheral adapter(s). Such adapter(s) may permit or facilitate connectivity between the device 100 and one or more of the processor(s) of an external device or network 200, 300, 400. For example, the peripheral adapter(s) may include a group of ports, which may include at least one of parallel ports, serial ports, Ethernet ports, V.35 ports, or X.21 ports. In certain embodiments, the parallel ports may comprise General Purpose Interface Bus (GPM), IEEE-1284, while the serial ports may include Recommended Standard (RS)-232, V.11, Universal Serial Bus (USB), Fire Wire, or IEEE-1394.

In one aspect, at least one of the network adapter(s) may be physically part of the communications system 130 and may functionally couple the user-wearable device 100 to one or more could networks 400 or computing devices 200, 300 via one or more wired or wireless transmission systems as exampled above. The information that is communicated by the at least one of the network adapter(s) may result from the implementation of one or more operations of a method in accordance with aspects of this disclosure. Such output may be any form of visual representation, including, but not limited to, textual, graphical, animation, audio, tactile, and the like. In certain scenarios, each of the user-wearable device(s) 100 may have substantially the same architecture as a computing device 300. In addition or in the alternative, the display unit(s) 150 may include functional elements, e.g., lights, such as light-emitting diodes; a display, such as a liquid crystal display (LCD), a plasma monitor, a light-emitting diode (LED) monitor, or an electrochromic monitor, as shown in FIG. 1, 150, combinations thereof, or the like, that may permit control of the operation of the user-wearable device 100, or may permit conveying or revealing the operational conditions of the user-wearable device 100.

In one aspect, the user-wearable device 100 may comprise a processor 125 or bus that represents one or more of several possible types of bus structures, including a memory bus or a memory controller, a peripheral bus, an accelerated graphics port, and a processor or local bus using any of a variety of bus architectures. As an illustration, such architectures may comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, a Peripheral Component Interconnect (PCI) bus, a PCI-Express bus, a Personal Computer Memory Card International Association (PCMCIA) bus, a Universal Serial Bus (USB), and the like. The processor 125 or bus, and all buses described herein may be implemented over a wired or wireless network connection and each of the subsystems, including the processor(s), the memory, which may be physically and functionally tied to the processor, and memory elements therein, and the I/O interface(s) may be contained within one or more remote computing devices or environment 200, 300, 400 at physically separate locations, connected through buses of this form, in effect implementing a fully distributed system. In certain embodiments, such a distributed system may implement the functionality described herein in a client-host or client-server configuration in which the method of treatment created by a health professional 700 or both, may be distributed between the example device 100 and at least one of the computing device(s) 200, 400, 300, and the example device 100 and at least one of the computing device(s) 200, 400, 300 containing a processor circuit 125 may execute such components and/or leverage such information.

The user-wearable device 100 may comprise a variety of computer-readable media. Computer-readable media may be any available media (transitory and non-transitory) that may be accessed by a computing device. In one aspect, computer-readable media may comprise computer non-transitory storage media (or computer-readable non-transitory storage media) and communications media. For example, computer-readable non-transitory storage media may be any available media that may be accessed by the user-wearable device 100, and may comprise, for example, both volatile and non-volatile media, and removable and/or non-removable media. In one aspect, the processor with memory component FIG. 3, 125 may comprise computer-readable media in the form of volatile memory, such as random access memory (RAM), and/or non-volatile memory, such as read-only memory (ROM).

The processor with memory component 125 may comprise functionality instructions storage and functionality information storage. The functionality instructions storage may comprise computer-accessible instructions that, in response to execution, by at least one of the processor(s) 125, may implement one or more of the functionalities of the disclosure controlling the detection and measurement systems therein as well as connected detection and measurement system devices 500, 600, 1600. The computer-accessible instructions may embody or may comprise one or more software components illustrated as treatment plan 1200. Treatment plan components 800, 900, 1000, 1100 would be suggested by a health professional 700 based on data of a patient 001 read by the systems of the example device 100 and optionally a nitric oxide sensing system 500, 600. The treatment plan components 800, 900, 1000, 1100 may also be viewed from a connected device 200 comprising software capable of displaying data related to the treatment plan.

Figure 5:
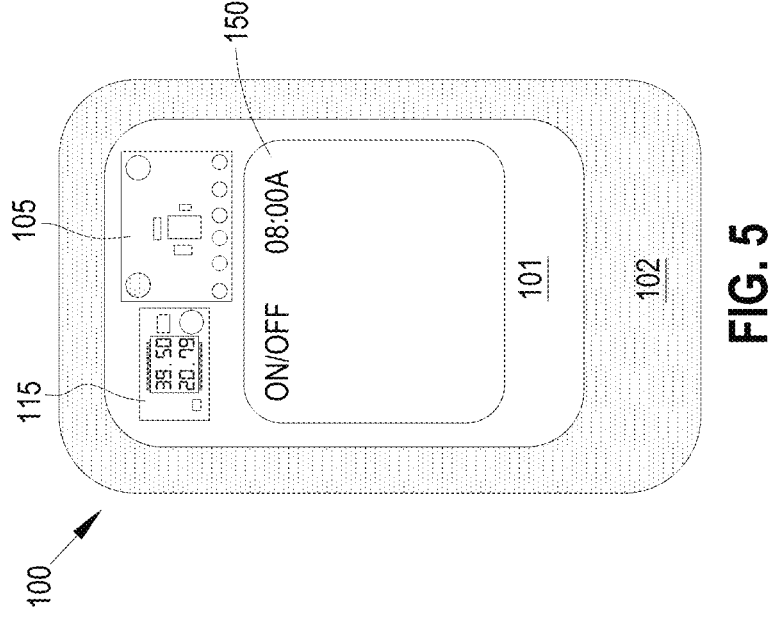
FIG. 5 illustrates a second embodiment of the front side of the example user-wearable device for monitoring user health data.

As illustrated in FIG. 5, the user-wearable device 100 front cover 101 may comprise systems such as the MEMs monitoring system 105 and breath humidity and temperature measurement system 115 on the exterior of the front cover 101, or partially integrated into the front cover 101 with components on the exterior of the front cover 101. As illustrated in FIG. 6, the user 001 may wear the user-wearable device 100 as shown on the upper chest. The user-wearable device 100 may be connected to other devices 200, 300 and/or cloud computing systems 400 in a wireless manner via systems described herein, as well as a contained 600 or separate 500 nitric oxide sensor system. A health professional 700 may access data generated by the user-wearable device 100 displayed on connected devices 200, 300. The health professional 700 may assess the user 001 for appropriateness of use of the device 100 and systems and methods FIG. 10 1500 described herein. The health professional may provide an initial treatment plan 1200 comprising immune-modulating herbs and biotic compounds 800, yoga practice and/or exercise plan 900, meditation practice 1000, and dietary information 1100 components. The user 001 may implement the initial treatment plan 1200 while wearing the user-wearable device 100, wherein the user-wearable device 100 will detect and measure user data, optionally store user data, or transfer data to connected devices, 200, 300, 400, wherein computer programs utilizing AI will execute ML models to continually refine the treatment plan 1200 to improve user 001 symptoms.

A treatment plan 1200 may comprise components such as recommendations for immune-modulating herbal and biotic supplements 800, yoga and exercise practices 900, meditation practices 1000, and nutritional and/or dietary information and suggestions 1100. Following such changes and practices of the treatment plan the user-wearable 100 continues to detect and measure user data, sending this data to an automated intelligence (AI) with machine learning (ML) capabilities which will continually refine the treatment plan and recommendations for components thereof.

Examples of immune-modulating herbal and biotic supplements 800 may include but not be limited to the following:

Anti-Inflammatory & Immune-Modulating Herbs
  Turmeric (*Curcuma longa*-Curcumin)
    Reduces airway inflammation (asthma).
    Downregulates NF-κB and TNF-α, helpful in Crohn's.
    Best taken with black pepper (piperine)+fat for absorption.

*Boswellia serrata* (Indian frankincense)
    Inhibits leukotrienes→reduces bronchial inflammation.
    Shown to lower intestinal inflammation in Crohn's/IBD trials.
  Licorice root (*Glycyrrhiza glabra*)
    Soothes airways (expectorant, demulcent).
    Protects gut mucosa, reduces ulceration.

Gut-Lung Axis Modulators
  Slippery Elm (*Ulmus rubra*)
    Mucilage coats GI tract→reduces Crohn's irritation.
    Soothes throat and airways in asthma-related coughing.
  Marshmallow root (Althaea *officinalis*)
    Similar mucilage effect: protects mucosa in lungs and gut.
  Aloe vera (inner gel, not latex)
    Anti-inflammatory for intestinal mucosa.
    Mild immune-balancing effect.

Antioxidant & Stress-Reducing Herbs
  Ashwagandha (Withania somnifera)
    Adaptogen: reduces cortisol (stress is a flare trigger for both diseases).
    Supports immune balance (Th1/Th2 modulation).
  Green tea (*Camellia sinensis*—EGCG)
    Antioxidant, reduces oxidative stress in lungs.
    May lower inflammatory cytokines in IBD.
  Holy Basil (Tulsi, *Ocimum sanctum*)
    Bronchodilator effect.
    Supports gut health & reduces stress-mediated flares.

Specific Respiratory+Gut Targeting Herbs
  Ginger (*Zingiber officinale*)
    Reduces airway constriction.
    Aids digestion, reduces bloating in Crohn's.
  Peppermint (*Mentha piperita*)
    Antispasmodic for GI tract.
    Clears nasal/airway passages.

Practical Formulations include but are not limited to:
  1. Tea blend (for daily calming+inflammation): Turmeric+ginger+tulsi+licorice root (mild, soothing).
  2. Capsule/extracts (standardized): *Boswellia*, curcumin, ashwagandha.
  3. Gut-soothing drink: Slippery elm or marshmallow root powder mixed with warm water before meals.

Immune-modulating herbal and biotic Supplements 800 may include pre- or postbiotic supplements. Postbiotic supplements may be applied or utilized through microinjections or through transdermal patches. These postbiotics can be safer than probiotics, as they are not live microbes yet retain immunomodulatory effects. Postbiotic microneedle patch(es) are one delivery method that includes a patch worn on the skin that has tiny, dissolvable needles made from safe materials. These needles painlessly poke just into the skin and then melt, leaving their medicine inside. Instead of using live bacteria, the patch delivers safe products made by good gut bacteria ("postbiotics"), such as but not limited to the following: butyrate and propionate, being molecules that calm inflammation; indole propionic acid (IPA), being molecules that protect the gut and lungs, improving gut barrier, reducing inflammation, and regulate regulatory T cells (Tregs), being an antioxidant and gut-brain axis modulator; pieces of friendly bacteria, being in one example, cell wall fragments, or paraprobiotics that gently train the immune system to modulate inflammatory pathways; and/or small immune-balancing proteins or peptides including but not limited to cytokines, for example TNF-α, IL-6, IL-17; and/or specialized pro-resolving mediators (SPMs), including resolvins and protectins that reduce chronic inflammation. Once delivered, these molecules enter the bloodstream and may help balance the immune system and reduce gut inflammation to decrease Crohn's symptoms and calm airway overreaction to improve asthma symptoms. In an example transdermal hydrogel patches deliver a sustained release of the small postbiotic or parabiotic molecules over hour(s) to day(s). The transdermal patch may be connected to the user-wearable device 100 which detects, monitors, and accumulates data on improvement or worsening symptoms and the AI/ML system automatically changes dosage and delivery rates of the molecules.

A yoga practice and/or exercise component 900 of the treatment plan 1200 includes suggested poses and exercises to improve lung capacity and airway relaxation, enhance vagal tone, digestion, and gut circulation, and reduce stress that is a common flare-up trigger for both asthma and Crohn's Disease. Recommended breathing practices and poses include the following:

Pranayama (Breathing Practices)
    a. Anulom Vilom (alternate nostril breathing): balances autonomic nervous system.
    b. Bhramari (humming bee breath): calms airway hyperreactivity, reduces stress.
    c. Diaphragmatic breathing: strengthens lungs, massages gut.
Asanas (Postures)
    a. Supta Baddha Konasana (Reclined Bound Angle Pose): opens chest, relaxes gut.
    b. Bhujangasana (Cobra Pose): expands lungs, stimulates digestion.
    c. Setu Bandhasana (Bridge Pose): improves circulation to chest & abdomen.
    d. Pawanmuktasana (Wind-relieving pose): relieves bloating & aids gut motility.
    e. Balasana (Child's Pose): reduces stress, eases abdominal discomfort.

Meditation or meditative practices 900/1000 as part of the treatment plan 1200 include guided meditation or Yoga Nidra which lowers cortisol, stabilizing both asthma and Crohn's inflammation. An example yoga/meditation session of thirty minutes may include a five minute Pranayama diaphragmatic breathing session, a ten minute asanas or postures session, a five minute Pranayama diaphragmatic breathing session, and ten minutes of meditation and/or relaxation poses.

A diet information or component 1100 of the treatment plan may include but not be limited to suggestions for eating foods that reduce inflammation, are gut-soothing, and airway friendly. These include but are not limited to: steamed and/or boiled vegetables including carrots, zucchini, and pumpkin; fruits and grains such as bananas, applesauce, oats, and white rice; including fatty-fish, either salmon or sardines, flax, and/or chia seeds in a diet for omega-3 oils; including turmeric and/or ginger in a diet; and including probiotic rich foods such as yogurt or kefir in a diet, if tolerated.

Each of these treatment plan 1200 components 800, 900, 1000, 1100 may be modified and/or refined over-time as the user-wearable device 100 collects data from the user 001 via AI/ML tools of the device 100 or connected software programs 200, 400, 300 forming an on-going treatment plan. A user may decide to adopt one component 800, 900, 1000, 1100 of a treatment plan 1200 in order to collect data on success of one component of the treatment plan 1200 or adopt two, three, or all components of the plan. Since data is collected over time by the user-wearable device 100 data may be linked to an activity 900, 1000, or intake of an immune-modulating herb or biotic 800 or diet item 1100 via a time component.

Components of a ML system or ML model, being a complete software system designed to automatically learn from data, make predictions, and improve over time, encompasses not only the machine learning model but also the data pipelines, being communication from the user-wearable device 100 to other computing systems 200, 400, 300, deployment infrastructure, being at least one processor(s) 125 and communication systems 130 of the user-wearable device 100 in addition to processors and communication systems of a connected device 300 and/or computer readable direction processed in a cloud environment 400, and data collection systems 105, 112, 115, 122, 500, 600 of the user-wearable device 100. An ML system may include: 1) data ingestion and preprocessing steps to collect, clean, and transform raw data into a format suitable for the ML model being housed on the user-wearable device 100 or connected devices 200, 300, 400; 2) the ML model, being an algorithm that learns patterns from the data to make predictions, classifications, and/or changes in an output, in the present example being changes to a treatment plan 1200, being housed on the user-wearable device 100 or connected devices 200, 300, 400; 3) a training pipeline or process of feeding data to the ML algorithm to "train" the model, iteratively adjusting its parameters to minimize errors; a deployment infrastructure, being the underlying architecture of the user-wearable device 100 or connected devices 200, 300, 400 that hosts the trained model, making it available for inference on new data being either a connected device 200, 400; monitoring and feedback loops, being tools and processes to track the model's performance in production, e.g. in this case improvement of symptoms of the user 001, housed on the user-wearable device 100 or connected devices 200, 300, 400. The data and refined treatment plan 1200 may be reviewed by a health professional 700 and/or the user 001 for review and adjustment as needed.

Figure 8:
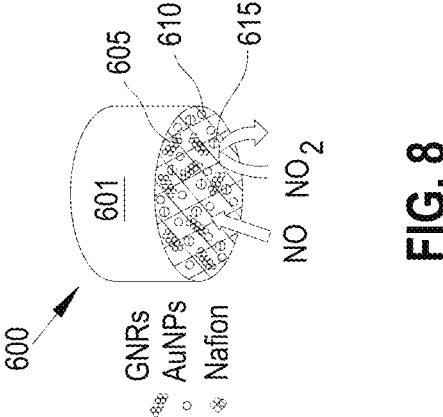
FIG. 8 illustrates an additional component, an electro-chemical nitric oxide sensor, of the example user-wearable device for monitoring user health data.
Figure 7:
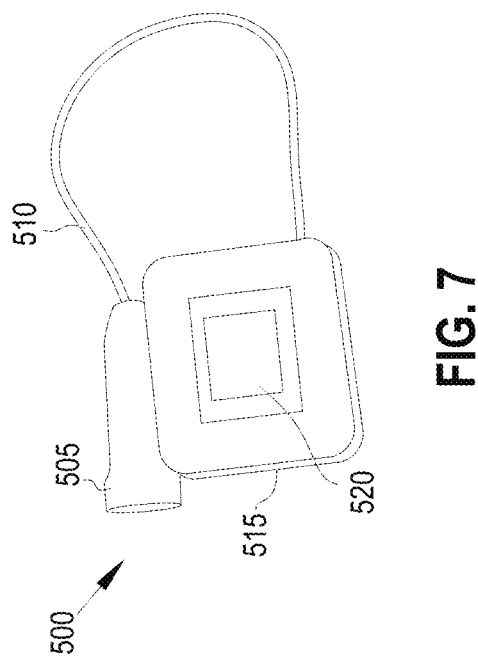
FIG. 7 illustrates an additional component, a fractional exhalation nitric oxide sensor, of the example user-wearable device for monitoring user health data.

Additional data on nitric oxide exhalation pertaining to the status of a user 001 may be collected by a nitric oxide (NO) sensor system 500 as illustrated by FIGS. 6-8. As illustrated in FIG. 7, 500 a separate, potentially wirelessly connected, nitric oxide exhalation sensor, being a fractional exhaled nitric oxide (FeNO) sensor for example, is a non-invasive, point-of-care breath test that measures NO of the user 001. The FeNO sensor 500 include a breathing apparatus 505 that is handheld and collects breath of a user and feeds it to, via a tube 510, the FeNO sensor 500 included in the device 515, wherein data is displayed on an electronic display 520 or via wireless connection to another device 100, 200, 300. Presence of nitric oxide in the breath of a user 001 is related to respiratory inflammation. A user 001 inhales, then exhales steadily at a controlled flow rate for about 10 seconds into the breathing apparatus 505. The device 500, 515 filters out environmental contaminants and moisture to ensure an accurate reading. FIG. 8 illustrates principals of an electrochemical nitric oxide (NO) sensor 600, FIG. 3, 127 which may be housed in the interior compartment 103 of the user-wearable device 100 or be a wirelessly connected separate device 600. The typical electrochemical NO sensor 127, 600 is composed of a housing 601 comprising a working electrode, a counter electrode, and a reference electrode. The electrochemical NO sensor 127, 600 operates by applying a voltage that is sufficiently positive (for oxidation) or negative (for reduction) to drive a redox reaction with the NO molecules. In the reaction at the electrode comprises NO diffuses from the environment into the sensor's electrolyte through a gas-permeable membrane 615, for example a Naflon membrane. The NO molecules then undergo an electrochemical reaction at the surface of the working electrode. The most common approach is the catalytic electro-oxidation of NO, which is often enhanced by immobilizing a catalyst, such as metalloporphyrins 605, 610 which in one example are gold nanorods 605 and gold nanoparticles 610, on the electrode surface. The transfer of electrons generates an electrical current that is directly proportional to the concentration of nitric oxide. The electrochemical NO sensor's 127, 600 circuitry measures and amplifies this current to provide a reading of the NO concentration which can be transferred to the user-wearable device 100 or other connected devices 200, 300, 400. Key components of the electrochemical NO sensor 300 include electrodes (not shown), being a working electrode where the NO reaction takes place. The material is critical for sensitivity and can include platinum, gold 605, 610, or carbon fiber, often modified with nanostructures or catalytic layers, a permselective membrane 615 which is the sensor's "gatekeeper," allowing NO to pass while blocking interfering electroactive species like nitrite, oxygen, and other biomolecules, and an electrolyte (not shown), in an internal solution which facilitates the transfer of charge between the electrodes.

Figure 9:
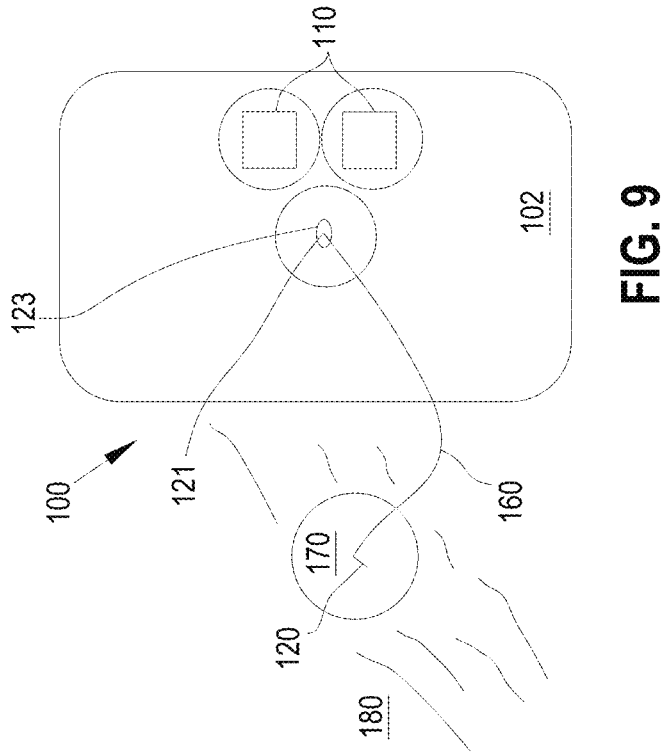
FIG. 9 presents a second embodiment of the back side of the example user-wearable device for monitoring user health data.

FIG. 9 illustrates an alternate design for the rear cover 102 of the user-wearable device. Electrodes 110 of the impedance system are illustrated as in FIG. 2. A support piece 123 supports a port 121 or passageway for a flexible tubing 160 which connects to a microneedle 120 of the interstitial fluid testing system 122. A small adhesive patch 170 with semi-permanent adhesive (not shown) on one side holds the microneedle 120 in place on the skin 180.

A method for reducing symptoms of asthma and/or Crohn's disease 1500 is presented in FIG. 10. The method comprises providing a user-wearable device to the patient 1505, wherein the user-wearable device comprises systems for performing one or more of the following: detecting wheezing, coughing, breathing, and other breath and lung sounds of the patient via a MEMS microphone system 1506; measuring impedance of the airways and lungs of the patient via a bioelectrical impedance analysis system 1507; measuring breath humidity and breath temperature of the patient via a breath humidity and breath temperature sensor system 1508; measuring at least one component of the patient's interstitial fluid via a connected interstitial fluid monitoring system comprising a microneedle 1509; optionally measuring exhaled nitric oxide of the user via an electronically connected exhaled nitric oxide measuring system 1510; and 1535 on the user-wearable device 100 or other connected devices 200, 400, 600: 1515 receiving data from the systems of the user-wearable device by at least one processor housed in the user-wearable device and storing data either on the user-wearable device or connected devices 200, 400, 600; and 1525 using at least one processor to compile the data received from the systems and detect trends to create an on-going treatment plan. The method may further comprise 1501 providing a questionnaire to a potential user to determine need of a user 001.

following manner with sensors detecting or measuring appropriate data, converting analog to digital data if needed, and sending the data to a processor 125 on the user-wearable device 100. Preprocessing of data, either by the processor 125 on the user-wearable device 100 or on connected devices 200, 300, 400 will include but not be limited to functions such as the following: 1) FFT or fast fourier transformation, being an algorithm that analyzes a signal to determine its frequency components over a given time period, FFT converts audio from the time domain (a series of amplitude values over time) into the frequency domain (the strength of various frequencies present), allowing for applications like sound analysis, audio compression, and creating frequency-based visualizations, often visualized as a frequency spectrum or graphic equalizer for example of the MEMS microphone 105 data collected; 2) impedance modeling of data collected from impedance system 110, 112; and 3) biosensor calibration for example from the breath humidity and breath temperature system 115, the interstitial fluid testing system 125, and/or the nitric oxide testing system 127, 500/600. A wireless BLE may send preprocessed data to a connected computer system 200, 300, 400 to analyze data for creation of a treatment plan. A prototype pathway example to create the user-wearable device 100 and method 1500 will entail the following.

1) Device Building
   1. Start with separate modules:
     Arduino/ESP32 programming system, MEMS mic, and bio-impedance front end
     Microneedle patch for interstitial fluid testing or use commercial electrochemical sensor
   2. Integrate separate modules into flexible printed circuit board (PCB) and incorporate with adhesive patch
   3. Miniaturize circuits, processor, electronics, power system, add BLE MCU, and create sealed wearable device 100

Asthma, Airway State Proxies
   Lung sounds (wheeze/cough) via sealed MEMS mic in a stethoscope-style cavity; band-limit ~100-2,500 Hz, 8-16 kHz sampling
   Respiratory rate & pattern via thoracic bioimpedance (chest) or accelerometry (chest/arm) to capture tidal motion/cough events
   Cough count, nocturnal activity, posture (supine), step rate (exertion)

Crohn's, Systemic & Contextual
   Interstitial fluid (ISF) inflammation via microneedle electrochemical sensing of CRP (+IL-6/TNF-$\alpha$)
   Skin temp, and HR/HRV for illness/stress context (optional PPG if power budget allows)
   Together, these provide a near-continuous picture: lung sounds+breathing for asthma; ISF inflammation trends for Crohn's 2) Hardware Design (Reference Stack)
Form Factor
   Upper chest patch (best for lung acoustics+bioimpedance); or upper arm band (easier wear, slightly worse acoustics)
   Biocompatible adhesive ring with soft overpatch; microneedle sits centrally or as a side "island"

Sensors & Front-Ends
   Acoustic: low-noise digital MEMS mic (e.g., 65 dB SNR, <35 dBA self-noise) in a 3-6 mm high cavity; anti-wind mesh; foam gasket to skin
   IMU: 6-axis with low-power wake-on-motion for cough peaks

EXAMPLES

Example I

In an example of the user-wearable device 100 and associated connected computer systems 200, 300, 400, the device will, in a non-limiting example, operate in the Bioimpedance (chest option): two small Ag/AgCl or stainless pads, 80-120 kHz injection; derive respiration waveform Microneedle ISF: gold-plated 3-electrode cell (working/ref/counter), passive wicking; electrochemical AFE (ADuCM355-class) for DPV/EIS reads of CRP immunosensor Temp: skin NTC or digital sensor near ISF site Compute & Radios MCU/BLE SoC (Cortex-M4F/M33, ≥512 kB Flash); on-device feature extraction to keep radio duty cycle low Audio ADC/codec if mic is analog; otherwise PDM-to-PCM on MCU Power 100-200 mAh LiPo coin pouch, fuel gauge, charger, DCDC+LDO Target>48-72 h mixed use (continuous IMU, duty-cycled audio, periodic ISF)

Enclosure

Skin-facing: ISO 10993 adhesive+liner; hydrophobic acoustic port; replaceable overpatch Microneedle module replaceable (daily) while electronics are reusable 3) Firmware & Sampling Plan Schedulers Acoustic windows: 30-60 s every 5-10 min at night; shorter windows by day or on symptom button press IMU: continuous low-rate (25-50 Hz) with event-triggered high-rate (200 Hz) around suspected coughs Bioimpedance (if chest): 30 s every 2-5 min for RR Microneedle/CRP: DPV/EIS once per hour (more during suspected flares) with blank/control pulse for drift On-Device Features Acoustic: spectrogram; wheeze band energy (400-1,600 Hz), tonal peak persistence, zero-crossing variance; cough envelope+spectral kurtosis.

IMU: respiration proxy, cough spikes (short, high-g peaks), posture, activity counts.

ISF: Faradaic peak height/area→CRP concentration via calibration curve; rolling median+EWMA trend.

Privacy: keep raw audio local; transmit features only unless clinician capture mode is enabled.

Example 2

Potential code for connecting the user-wearable device 100 sensor system data to cloud FIG. 6, 400 or other connected devices 200, 300, 500, 600 includes the following.

```
openapi: 3.0.3
info:
    title: Asthma-Crohn's Wearable API
    description: REST API for wearable-to-cloud pipeline
        (sensor data, symptom diary, alerts).
    version: 1.0.0
    servers:
        url: https://api.asthma-crohns-cloud.com/v1
        description: Production server
        url:   https://sandbox.api.asthma-crohns-cloud.com/
            v1
        description: Sandbox server for testing
    paths:
        /patients:
            post:
                summary: Register a new patient
                operationId: createPatient
```

```
                requestBody:
                    required: true
                    content:
                        application/json:
                            schema:
                                $ref: "#/components/schemas/Patient"
                responses:
                    "201":
                        description: Patient registered successfully
                        content:
                            application/json:
                                schema:
                                    $ref: "#/components/schemas/Patient"
        /patients/{patientId}/readings:
            post:
                summary: Upload sensor readings from wearable
                operationId: uploadReadings
                parameters:
                    in: path
                    name: patientId
                    required: true
                    schema:
                        type: string
                requestBody:
                    required: true
                    content:
                        application/json:
                            schema:
                                $ref: "#/components/schemas/SensorData"
                responses:
                    "201":
                        description: Data uploaded successfully
            get:
                summary: Retrieve recent readings
                operationId: getReadings
                parameters:
                    in: path
                    name: patientId
                    required: true
                    schema:
                        type: string
                    in: query
                    name: limit
                    schema:
                        type: integer
                        default: 50
                responses:
                    "200":
                        description: List of recent sensor readings
                        content:
                            application/json:
                                schema:
                                    type: array
                                    items:
                                        $ref: "#/components/schemas/SensorData"
        /patients/{patientId}/symptoms:
            post:
                summary: Submit symptom diary entry
                operationId: submitSymptoms
                parameters:
                    in: path
                    name: patientId
                    required: true
                    schema:
                        type: string
```

```
requestBody:
    required: true
    content:
        application/json:
            schema:
                $ref: "#/components/schemas/SymptomEntry"
    responses:
        "201":
            description: Symptom entry saved
/patients/{patientId}/alerts:
    get:
        summary: Fetch active alerts
        operationId: getAlerts
        parameters:
            in: path
            name: patientId
            required: true
            schema:
                type: string
        responses:
            "200":
                description: List of alerts for the patient
                content:
                    application/json:
                        schema:
                            type: array
                            items:
                                $ref: "#/components/schemas/Alert"
components:
    schemas:
        Patient:
            type: object
            properties:
                id:
                    type: string
                name:
                    type: string
                dob:
                    type: string
                    format: date
                gender:
                    type: string
                    enum: [male, female, other]
        SensorData:
            type: object
            properties:
                timestamp:
                    type: string
                    format: date-time
                respiratory:
                    type: object
                    properties:
                        wheezeScore:
                            type: number
                        coughEvents:
                            type: integer
                        respRate:
                            type: number
                inflammation:
                    type: object
                    properties:
                        crp:
                            type: number
```

```
                        il6:
                            type: number
                        tnfAlpha:
                            type: number
                motion:
                    type: object
                    properties:
                        activityLevel:
                            type: string
                            enum: [rest, light, moderate, intense]
        SymptomEntry:
            type: object
            properties:
                timestamp:
                    type: string
                    format: date-time
                asthmaSymptoms:
                    type: string
                    example: "Shortness of breath during exercise"
                crohnsSymptoms:
                    type: string
                    example: "Abdominal pain after meal"
                notes:
                    type: string
        Alert:
            type: object
            properties:
                id:
                    type: string
                type:
                    type: string
                    enum: [asthma, crohns, combined]
                severity:
                    type: string
                    enum: [low, medium, high, critical]
                message:
                    type: string
                timestamp:
                    type: string
                    format: date-time
```

Example 3

In a first step of the method 1500, 1501, a user may be evaluated for need for treatment method 1500 and user-wearable device 100. The following is an example questionnaire which may be used to determine eligibility by a healthcare professional. There will be an app which is built and will comprise a patient login module. Following patient enrollment and/or account creation and login the next step will be an initial asthma and Crohn's Disease screening questionnaire. Based on the patient filled questionnaire, uploaded prick tests, subsequent blood lab reports, and/or fecal biomarkers data, the healthcare professional can pre-scribe or approve the user-wearable monitoring sensor device 100 for patients/users 001. It is noted that some genes, particularly IL23R, IL4, IL13, STAT6, and TNFAIP3, have overlapping roles in both asthma and Crohn's disease, mainly through their regulation of immune pathways like Th2, Th17, and NF-κB. The following is an example questionnaire that may be displayed graphically with option to input data via touchscreen. Optionally the questionnaire may be written or otherwise presented to a potential patient or user 001.

Asthma Screening Questionnaire

Patient Information

- Name: _____
- Date of Birth: _____
- Gender: ☐ Male ☐ Female ☐ Other
- Date: _____

*Section 1: Symptom Checklist*

Please check all the symptoms you have experienced in the past 12 months.

1. Wheezing (a high-pitched sound when exhaling)
   ☐ Yes ☐ No
2. Shortness of breath (feeling like you can't breathe easily)
   ☐ Yes ☐ No
3. Chest tightness (like a feeling of pressure or constriction)
   ☐ Yes ☐ No
4. Frequent coughing (especially at night or early morning)
   ☐ Yes ☐ No
5. Coughing after exercise or physical activity
   ☐ Yes ☐ No
6. Coughing with exposure to cold air or allergens
   ☐ Yes ☐ No
7. Symptoms worsening during the night
   ☐ Yes ☐ No

*Section 2: Triggers and Environmental Factors*

Please answer the following questions about your asthma triggers and environmental factors.

1. Do your symptoms get worse with any of the following? (Check all that apply)
- ☐ Dust
- ☐ Pollen
- ☐ Mold
- ☐ Pets (cats, dogs, etc.)
- ☐ Strong odors (perfumes, cleaning products)
- ☐ Exercise or physical activity
- ☐ Weather (cold or hot air)
- ☐ Tobacco smoke
- ☐ Pollution
- ☐ Respiratory infections (cold or flu)
- ☐ Other: _____

- . Have you ever had an allergic reaction (e.g., rash, swelling, etc.) to any of the following?
- ☐ Dust
- ☐ Pollen
- ☐ Food (e.g., nuts, shellfish)
- ☐ Insect stings or bites
- ☐ Other allergens (e.g., latex, medications): _____

*Section 3: Past Medical History*

1. Have you ever been diagnosed with asthma or any other lung conditions (e.g., chronic bronchitis, COPD)?

☐ Yes ☐ No

If yes, when were you diagnosed? _____

2. Have you ever had any of the following tests? (Check all that apply)

☐ Spirometry (lung function test)

☐ Peak flow monitoring

☐ Chest X-ray or CT scan

☐ Allergy tests (skin prick or blood test)

☐ Bronchial challenge test (methacholine test)

3. Have you used any of the following medications for your breathing problems? (Check all that apply)

☐ Inhalers (e.g., albuterol, corticosteroids)

☐ Oral medications (e.g., antihistamines, leukotriene modifiers)

☐ Other: _____

*Section 4: Lifestyle and Symptoms Severity*

1. How often do you experience symptoms (wheezing, coughing, shortness of breath)?

☐ Rarely

☐ Occasionally

☐ Frequently

☐ Constantly

2. Do your symptoms affect your daily activities (work, school, exercise)?

☐ Yes ☐ No

If yes, please describe: _____

3. How many times in the past 12 months have you needed to visit the emergency room for asthma or breathing issues?

☐ None

☐ 1–2 times

☐ 3–5 times

☐ More than 5 times

4. Have you ever been hospitalized due to asthma or breathing problems?

☐ Yes ☐ No

If yes, when? _____

*Section 5: General Health Information*

*1. Are you currently taking any medications for other health conditions?*

*☐ Yes ☐ No*

*If yes, please list:* _____

*2. Have you ever been diagnosed with other chronic conditions, such as:*

- Obesity
- ☐ Diabetes
- ☐ Gastroesophageal reflux disease (GERD)
- ☐ Sinus issues (e.g., chronic sinusitis)
- ☐ Allergic rhinitis (hay fever)

Section 6: Genetic and Research-Related Questions

Please answer the following questions about genetic factors and family history of asthma:

*Family History*

Please answer the following questions about your family's health.

1. Do any of your family members have asthma?

☐ Yes ☐ No

If yes, who? _____

2. Do you have a family history of the following? (Check all that apply)

☐ Asthma

☐ Hay fever (allergic rhinitis)

☐ Eczema

☐ Other allergic diseases (e.g., food allergies)

3. Do you know if there are any known genetic conditions related to asthma in your family?

☐ Yes ☐ No

If yes, please describe: _____

4. Is there a history of asthma in any other relatives outside of your immediate family (e.g., grandparents, cousins)?

☐ Yes ☐ No

If yes, who? _____

5. Do you have a family history of other autoimmune conditions?
☐ Yes ☐ No
If yes, check all that apply:

- ☐ Rheumatoid arthritis
- Crohn's Disease
- ☐ Celiac disease
- ☐ Lupus
- ☐ Type 1 diabetes
- ☐ Multiple sclerosis
- ☐ Psoriasis
- ☐ Other autoimmune conditions: _____

If Crohn's Disease is selected then the following questionnaire should appear:

1.. Do any of your immediate family members have Crohn's disease or other inflammatory bowel diseases (IBD)?

☐ Yes ☐ No

If yes, who? _____

2.. Do any of your family members have both asthma and Crohn's disease?

☐ Yes ☐ No

If yes, please specify: _____

3. Have you been tested for any asthma-related genes or genetic markers in the past?

□ Yes □ No

If yes, were any asthma-related genes identified? _____

4. Would you be willing to participate in genetic testing to help assess your risk for asthma or allergic conditions?

□ Yes □ No

5. Do you experience any of the following symptoms of Crohn's disease? (Check all that apply)

□ Chronic diarrhea

□ Abdominal pain or cramping

□ Blood in stool

□ Unexplained weight loss

□ Fatigue

□ Nausea or vomiting

□ Loss of appetite

□ Other gastrointestinal symptoms: _____

6. Have you ever used any of the following medications for Crohn's disease? (Check all that apply)

□ Anti-inflammatory drugs (e.g., corticosteroids)

□ Immunosuppressants (e.g., azathioprine)

□ Biologic therapies (e.g., TNF inhibitors like infliximab)

□ Other: _____

7. Do any of the following trigger your asthma symptoms? (Check all that apply)

□ Dairy products

□ Gluten or wheat

□ Fatty or fried foods

□ Spicy foods

☐ Alcohol

☐ Specific foods (e.g., nuts, shellfish, etc.)

8. Do your asthma symptoms worsen after a flare-up of Crohn's disease?

☐ Yes ☐ No

If yes, please describe the pattern: _____

9. Do you find that your asthma symptoms improve when your Crohn's disease symptoms are controlled?

☐ Yes ☐ No

If yes, please explain: _____

10. Have you noticed that certain medications for Crohn's disease trigger or worsen your asthma symptoms?

☐ Yes ☐ No

If yes, which medications?

☐ Corticosteroids (e.g., prednisone)

☐ Immunosuppressants (e.g., azathioprine, methotrexate)

☐ Biologic therapies (e.g., infliximab, adalimumab)

☐ Antibiotics (e.g., for infections related to Crohn's disease)

☐ Other medications: _____

11. Do you have a history of using non-steroidal anti-inflammatory drugs (NSAIDs) for pain or inflammation?

☐ Yes ☐ No

12. If yes, did NSAIDs worsen your asthma or Crohn's symptoms?

☐ Yes ☐ No

13. Have you experienced any asthma flare-ups after undergoing gastrointestinal procedures or treatments related to Crohn's disease?

☐ Yes ☐ No

If yes, what procedure or treatment was it? _____

14. Have you noticed a correlation between your asthma symptoms and changes in your Crohn's disease symptoms during the following? (Check all that apply)

☐ Changes in diet (e.g., flare-ups or dietary restrictions)

☐ Environmental changes (e.g., new home, travel)

☐ Exposure to allergens (e.g., pollen, mold)

☐ Cold weather

☐ Physical activity or exercise

☐ Stress

15. Do you find that stress worsens both your asthma and Crohn's disease symptoms?

☐ Yes ☐ No

If yes, please describe how stress impacts your symptoms: _____

16. Have you experienced more frequent asthma symptoms during periods of illness or flare-ups of Crohn's disease?

☐ Yes ☐ No

If yes, please describe the relationship: _____

17. Have you recently made any significant changes to your diet or lifestyle that have impacted both asthma and Crohn's disease?

☐ Yes ☐ No

If yes, please explain: _____

Various embodiments of the disclosure may take the form of an entirely or partially hardware embodiment, an entirely or partially software embodiment, or a combination of software and hardware (e.g., a firmware embodiment). Furthermore, as described herein, various embodiments of the disclosure (e.g., methods and systems) may take the form of a computer programming product comprising a computer-readable non-transitory storage medium having computer-accessible instructions (e.g., computer-readable and/or computer-executable instructions) such as computer software, encoded or otherwise embodied in such storage medium. Those instructions may be read or otherwise accessed and executed by one or more processor circuits to perform or permit the performance of the operations described herein. The instructions may be provided in any suitable form, such as source code, compiled code, interpreted code, executable code, static code, dynamic code, assembler code, combinations of the foregoing, and the like. Any suitable computer-readable non-transitory storage medium may be utilized to form the computer program product. For instance, the computer-readable medium may include any tangible non-transitory medium for storing information in a form readable or otherwise accessible by one or more computers or processor(s) functionally coupled thereto. Non-transitory storage media may include read-only memory (ROM); random access memory (RAM); magnetic disk storage media; optical storage media; flash memory, etc.

Embodiments of the operational environments and methods (or techniques) are described herein with reference to block diagrams and flowchart illustrations of methods, systems, apparatuses, and computer program products. It may be understood that each block of the block diagrams and flowchart illustrations, and combinations of blocks in the block diagrams and flowchart illustrations, respectively, may be implemented by computer-accessible instructions. In certain implementations, the computer-accessible instructions may be loaded or otherwise incorporated into a general purpose computer, special purpose computer, or other programmable information processing apparatus to produce a particular machine, such that the operations or functions specified in the flowchart block or blocks may be implemented in response to execution at the computer or processing apparatus.

Unless otherwise expressly stated, it is in no way intended that any protocol, procedure, process, or method set forth herein be construed as requiring that its acts or steps be performed in a specific order. Accordingly, where a process or a method claim does not actually recite an order to be followed by its acts or steps or it is not otherwise specifically recited in the claims or descriptions of the subject disclosure that the steps are to be limited to a specific order, it is in no way intended that an order be inferred, in any respect. This holds for any possible non-express basis for interpretation, including: matters of logic with respect to the arrangement of steps or operational flow; plain meaning derived from grammatical organization or punctuation; the number or type of embodiments described in the specification or annexed drawings, or the like.

As used in this application, the terms "component," "environment," "system," "architecture," "interface," "unit," "module," "pipe," and the like are intended to refer to a computer-related entity or an entity related to an operational apparatus with one or more specific functionalities. Such entities may be either hardware, a combination of hardware and software, software, or software in execution. As an example, a component may be, but is not limited to being, a process running on a processor, a processor, an object, an executable portion of software, a thread of execution, a program, and/or a computing device. For example, both a software application executing on a computing device containing a processor circuit and the computing device may be a component. One or more components may reside within a process and/or thread of execution. A component may be localized on one computing device or distributed between two or more computing devices. As described herein, a component may execute from various computer-readable non-transitory media having various data structures stored thereon. Components may communicate via local and/or remote processes in accordance, for example, with a signal (either analogic or digital) having one or more data packets (e.g., data from one component interacting with another component in a local system, distributed system, and/or across a network such as a wide area network with other systems via the signal). As another example, a component may be an apparatus with specific functionality provided by mechanical parts operated by electric or electronic circuitry that is controlled by a software application or firmware application executed by a processor circuit, wherein the processor may be internal or external to the apparatus and may execute at least a part of the software or firmware application. As yet another example, a component may be an apparatus that provides specific functionality through electronic components without mechanical parts, and the electronic components may include a processor therein to execute software or firmware that provides, at least in part, the functionality of the electronic components. In certain embodiments, components may communicate via local and/or remote processes in accordance, for example, with a signal (either analog or digital) having one or more data packets (e.g., data from one component interacting with another component in a local system, distributed system, and/or across a network such as a wide area network with other systems via the signal). In other embodiments, components may communicate or otherwise be coupled via thermal, mechanical, electrical, and/or electromechanical coupling mechanisms (such as conduits, connectors, combinations thereof, or the like). An interface may include input/output (I/O) components as well as associated processors, applications, and/or other programming components. The terms "component," "environment," "system," "architecture," "interface," "unit," "module," and "pipe" may be utilized interchangeably and may be referred to collectively as functional elements.

As utilized in this disclosure, the term "processor" may refer to any computing processing unit or device comprising single-core processors; single processors with software multithread execution capability; multi-core processors; multi-core processors with software multithread execution capability; multi-core processors with hardware multithread technology; parallel platforms; and parallel platforms with distributed shared memory. Additionally, a processor may refer to an integrated circuit (IC), an application-specific integrated circuit (ASIC), a digital signal processor (DSP), a field programmable gate array (FPGA), a programmable logic controller (PLC), a complex programmable logic device (CPLD), a microcontroller unit (MCU), a system of a chip (SoC), analog to digital (ADC) processor, a discrete gate or transistor logic, discrete hardware components, or any combination thereof designed to perform the functions described herein. A processor may be implemented as a combination of computing processing units. In certain embodiments, processors may utilize nanoscale architectures such as, but not limited to, molecular and quantum-dot based transistors, switches, and gates, to optimize space usage or enhance the performance of user equipment or other electronic equipment.

As used herein, a singular term may include multiple objects. As used herein, a single element may include multiple such elements. For example, the term "computer" may include a single computer or multiple computers. The phrase "a computer that stores data and runs software," may include a single computer that both stores data and runs software, a first computer that stores data and a second computer that runs software, or multiple computers that together store data and run software, where at least one of the multiple computers stores data and at least one of the multiple computers runs software. For example, the term "processor" may include a single processor or multiple processors. The phrase "a processor that stores data and runs software," may include a single processor that both stores data and runs software, a first processor that stores data and a second processor that runs software, or multiple processors that together store data and run software, where at least one of the multiple processors store data and at least one of the multiple processors runs software. An implementation comprising multiple processors may configure each particular processor of the multiple processors to exclusively execute only a particular task assigned to that particular processor. An implementation comprising multiple processors may configure each particular processor of the multiple processors to execute any task of multiple tasks assigned to that particular processor by a scheduler such that a different task may be assigned to different processors at different times. As used herein in an apparatus or a computer-readable medium, "at least one" object rather than or in addition to a single object may perform the claimed operations. For example, "a computer-readable medium" may be construed as "at least one computer-readable medium," and "an apparatus comprising a processor and a memory" may be construed as "a system comprising processing circuitry and a memory subsystem," or "a system comprising processing circuitry and memory" (where memory lacks the article 'a'). It should be noted that a skilled person would understand that "processing circuitry" may include a single processor or multiple processors. Similarly, "memory subsystem" or "memory" (lacking an article) may include a single memory unit or multiple memory unit.

In addition, in the present specification and annexed drawings, terms such as "store," "storage," "data store," "data storage," "memory," "repository," and substantially any other information storage component relevant to the operation and functionality of a component of the disclosure, refer to "memory components," entities embodied in a "memory," or components forming the memory. It may be appreciated that the memory components or memories described herein embody or comprise non-transitory computer storage media that may be readable or otherwise accessible by a computing device. Such media may be implemented in any methods or technology for storage of information such as computer-readable instructions, information structures, program modules, or other information objects. The memory components or memories may be either volatile memory or non-volatile memory, or may include both volatile and non-volatile memory. In addition, the memory components or memories may be removable or non-removable, and/or internal or external to a computing device or component. Examples of various types of non-transitory storage media may include hard-disc drives, zip drives, CD-ROMs, digital versatile disks (DVDs) or other optical storage, magnetic cassettes, magnetic tape, magnetic disk storage or other magnetic storage devices, flash memory cards or other types of memory cards, cartridges, or any other non-transitory medium suitable to retain the desired information and which may be accessed by a computing device.

As an illustration, non-volatile memory may include read only memory (ROM), programmable ROM (PROM), electrically programmable ROM (EPROM), electrically erasable programmable ROM (EEPROM), or flash memory. Volatile memory may include random access memory (RAM), which acts as external cache memory. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), and direct Rambus RAM (DRRAM). The disclosed memory components or memories of the operational or computational environments described herein are intended to include one or more of these and/or any other suitable types of memory.

Conditional language, such as, among others, "may," "could," "might," or "may," unless specifically stated otherwise, or otherwise understood within the context as used, is generally intended to convey that certain implementations could include, while other implementations do not include, certain features, elements, and/or operations. Thus, such conditional language generally is not intended to imply that features, elements, and/or operations are in any way required for one or more implementations or that one or more implementations necessarily include logic for deciding, with or without user input or prompting, whether these features, elements, and/or operations are included or are to be performed in any particular implementation.

Many suitable methods and corresponding materials to make each of the individual parts of implementation apparatus are known in the art. One or more implementation part may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described hereinabove may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112(f). Specifically, any use of "step of" in the claims herein is not intended to invoke the provisions of 35 U.S.C. § 112(f). Elements recited in means-plus-function format are intended to be construed in accordance with 35 U.S.C. § 112(f).

The phrases "connected to," "coupled to" and "in communication with" refer to any form of interaction between two or more entities, including mechanical, electrical, chemical, magnetic, electromagnetic, fluid, and thermal interaction. Two components may be functionally coupled to each other even though they are not in direct contact with each other. The terms "abutting" or "in mechanical union" refer to items that are in direct physical contact with each other, although the items may not necessarily be attached together.

Similarly, it should be appreciated that in the above description, various features are sometimes grouped together in a single implementation, Figure, or description thereof for the purpose of streamlining the disclosure. This method of disclosure, however, is not to be interpreted as reflecting an intention that any claim in this or any application claiming priority to this application require more features than those expressly recited in that claim. Rather, as the following claims reflect, inventive aspects may lie in a combination of fewer than all features of any single foregoing disclosed implementation. Thus, the claims following this Detailed Description are hereby expressly incorporated into this Detailed Description, with each claim standing on its own as a separate implementation. This disclosure is intended to be interpreted as including all permutations of the independent claims with their dependent claims.

What has been described herein in the present specification and annexed drawings includes examples of systems, devices, and techniques that may provide emergency responses within a defined coverage area. It is, of course, not possible to describe every conceivable combination of elements and/or methods for purposes of describing the various features of the disclosure, but it may be recognized that many further combinations and permutations of the disclosed features are possible. Accordingly, it may be apparent that various modifications may be made to the disclosure without departing from the scope or spirit thereof. In addition, or in the alternative, other embodiments of the disclosure may be apparent from consideration of the specification and annexed drawings, and practice of the disclosure as presented herein. It is intended that the examples put forward in the specification and annexed drawings be considered, in all respects, as illustrative and not restrictive. Although specific terms are employed herein, they are used in a generic and descriptive sense only and not for purposes of limitation.

What is claimed is:

1. A method for treating at least one of asthma and Crohn's or inflammatory bowel disease (IBD) in a patient with need for treatment thereof, the method comprising the steps of:

i. detecting wheezing, coughing, breathing, and other breath, and lung sounds of the patient via a MEMS microphone system housed in a user-wearable device;

ii. measuring impedance of the airways and lungs of the patient via a bioelectrical impedance analysis system housed in the user-wearable device;

iii. measuring breath humidity and breath temperature of the patient via a breath humidity and breath temperature sensor system housed in the user-wearable device;

iv. measuring at least one component of the patient's interstitial fluid via an interstitial fluid monitoring system housed in the user-wearable device and comprising a microneedle connected to the user-wearable device, wherein the one component is selected from at least one of CRP, TNF-α, IL-6, and Calprotectin; and v. receiving and compiling data from each system of the user-wearable device to produce a systems' data package;

vi. creating, by an individual user adjustable treatment program of the user-wearable device, based on the systems' data package received over time, an ongoing treatment plan for treatment of a disease or condition consisting of asthma and at least one of Crohn's and IBD, wherein the ongoing treatment plan consists of suggestions for implementation of at least one of diet changes, yoga practice, meditation practice, and use of immune-modulating herbs or biotics by the patient; and vii. implementing the ongoing treatment plan by the patient; and viii. following implementation of the ongoing treatment plan, adjusting the ongoing treatment plan based on a new systems' data package for ongoing treatment of a disease or condition consisting of asthma and at least one of Crohn's and IBD.

2. The method of claim 1 further comprising measuring exhaled nitric oxide of the user via an exhaled nitric oxide measuring system and supplying data from the exhaled nitric oxide measuring system to at least one of the systems' data package and the new systems' data package.

3. The method of claim 2, wherein the exhaled nitric oxide measuring system comprises a fractional exhaled nitric oxide testing device.

4. The method of claim 2, wherein the exhaled nitric oxide measuring system comprises an electrochemical sensor capable of detecting nitric oxide.

5. The method of claim 1 further comprising a first step of supplying by the patient at least one of health data, health history, medication history, diet information, environmental exposure data, stress data, and lifestyle data to determine whether the patient is in need of the treatment for at least one of asthma and Crohn's or IBD.

6. The method of claim 1 further comprising supplying fecal biomarker data of the patient to at least one of the systems' data package and the new systems' data package.

\* \* \* \* \*